(12) United States Patent
Zarkh et al.

(10) Patent No.: US 8,295,577 B2
(45) Date of Patent: Oct. 23, 2012

(54) METHOD AND APPARATUS FOR GUIDING A DEVICE IN A TOTALLY OCCLUDED OR PARTLY OCCLUDED TUBULAR ORGAN

(76) Inventors: Michael Zarkh, Givat Shmuel (IL); Klaiman Moshe, Gadera (IL)

( * ) Notice: Subject to any disclaimer, the term of this patent is extended or adjusted under 35 U.S.C. 154(b) by 593 days.

(21) Appl. No.: 12/446,459

(22) PCT Filed: Oct. 22, 2006

(86) PCT No.: PCT/IL2006/001214
§ 371 (c)(1), (2), (4) Date: Jan. 10, 2010

(87) PCT Pub. No.: WO2008/050315
PCT Pub. Date: May 2, 2008

(65) Prior Publication Data
US 2010/0312100 A1 Dec. 9, 2010

(51) Int. Cl.
*G06K 9/00* (2006.01)
(52) U.S. Cl. .......... 382/132; 382/284
(58) Field of Classification Search .......... 382/128, 382/130, 131, 132, 284, 294
See application file for complete search history.

(56) References Cited

U.S. PATENT DOCUMENTS

| | | | |
|---|---|---|---|
| 4,263,916 A | 4/1981 | Brooks et al. | 128/654 |
| 4,889,128 A | 12/1989 | Millar | 128/662.06 |
| 5,089,005 A | 2/1992 | Harada | 606/194 |
| 5,175,773 A | 12/1992 | Garreau et al. | 382/6 |
| 5,203,777 A | 4/1993 | Lee | 604/280 |
| 5,207,226 A | 5/1993 | Bailin et al. | 128/661.08 |
| 5,289,373 A * | 2/1994 | Zarge et al. | 600/434 |
| 5,357,550 A | 10/1994 | Asahina et al. | 378/98.5 |
| 5,446,800 A | 8/1995 | Briggs et al. | 382/128 |
| 5,583,902 A | 12/1996 | Bae | 378/8 |
| 5,699,799 A | 12/1997 | Xu et al. | 128/653.1 |
| 5,718,724 A | 2/1998 | Goicoechea et al. | 623/1 |
| 5,729,129 A | 3/1998 | Acker | 324/207.12 |
| 5,732,707 A | 3/1998 | Widder et al. | 128/661.08 |
| 5,734,384 A | 3/1998 | Yanof et al. | 345/424 |
| 5,840,025 A | 11/1998 | Ben Haim | 600/424 |
| 5,912,945 A | 6/1999 | Da Silva et al. | 378/205 |

(Continued)

FOREIGN PATENT DOCUMENTS

DE 100 47 314 A1 4/2001

(Continued)

OTHER PUBLICATIONS

Penney G P et al "A Comparison of Similarity Measures for Use in 2-D-3-D Medical Image Registration" IEEE Transactions on Medical Imaging, IEEE Service Center, Piscataway, NJ, US, vol. 17, No. 4. pp. 586-595, Aug. 1998.

(Continued)

*Primary Examiner* — Andrew W Johns

(57) ABSTRACT

An apparatus and method for detecting, tracking and registering a device (218) within a tubular organ (210) of a subject. The devices include guide wire (216) tip or therapeutic devices, and the detection and tracking uses fluoroscopic images taken prior to or during a catheterization operation. The devices are fused with images or projections of models depicting tile tubular organs. Tile method and apparatus are used for treating chronic total occlusion or near total occlusion situations, by navigating a driller along the tubular organ (210) proximally to the occlusion point, in areas which are not viewable in an angiogram, and optionally enabling the penetration of the occlusion in a preferred area.

14 Claims, 8 Drawing Sheets

U.S. PATENT DOCUMENTS

| | | | | |
|---|---|---|---|---|
| 5,978,439 | A | 11/1999 | Koppe et al. | 378/8 |
| 6,027,460 | A | 2/2000 | Shturman | 600/585 |
| 6,047,080 | A | 4/2000 | Chen et al. | 382/128 |
| 6,094,591 | A | 7/2000 | Foltz et al. | 600/419 |
| 6,167,296 | A | 12/2000 | Shahidi | 600/427 |
| 6,190,353 | B1 | 2/2001 | Makower et al. | 604/95 |
| 6,195,577 | B1 | 2/2001 | Truwit et al. | 600/411 |
| 6,231,518 | B1 | 5/2001 | Grabek et al. | 600/508 |
| 6,233,476 | B1 | 5/2001 | Strommer et al. | 600/424 |
| 6,246,898 | B1 | 6/2001 | Vesly et al. | 600/424 |
| 6,249,695 | B1 | 6/2001 | Damadian | 600/427 |
| 6,290,673 | B1 | 9/2001 | Shanley | 604/102.02 |
| 6,301,498 | B1 | 10/2001 | Greenberg et al. | 600/425 |
| 6,317,621 | B1 | 11/2001 | Graumann et al. | 600/424 |
| 6,332,034 | B1 | 12/2001 | Makram-Ebeid et al. | 382/128 |
| 6,334,864 | B1 | 1/2002 | Amplatz et al. | 606/200 |
| 6,351,513 | B1 | 2/2002 | Bani-Hashemi et al. | 378/8 |
| 6,381,350 | B1 | 4/2002 | Klingensmith et al. | 382/128 |
| 6,381,483 | B1 | 4/2002 | Hareyama et al. | 600/407 |
| 6,385,332 | B1 | 5/2002 | Zahalka et al. | 382/128 |
| 6,389,104 | B1 | 5/2002 | Bani-Hashemi et al. | 378/98.12 |
| 6,463,309 | B1 | 10/2002 | Ilia | 600/310 |
| 6,470,207 | B1 | 10/2002 | Simon et al. | 600/426 |
| 6,501,848 | B1 | 12/2002 | Carroll et al. | 382/128 |
| 6,503,203 | B1 | 1/2003 | Rafter et al. | 600/458 |
| 6,505,064 | B1 | 1/2003 | Liu et al. | 600/420 |
| 6,535,756 | B1 | 3/2003 | Simon et al. | 600/424 |
| 6,544,178 | B1 | 4/2003 | Grenon et al. | 600/443 |
| 6,544,230 | B1 | 4/2003 | Flaherty et al. | 604/164.12 |
| 6,669,635 | B2 | 12/2003 | Kessman et al. | 600/437 |
| 6,669,645 | B2 | 12/2003 | Narimatsu et al. | 600/485 |
| 6,709,444 | B1 | 3/2004 | Makower | 606/198 |
| 6,748,259 | B1 | 6/2004 | Benaron et al. | 600/476 |
| 6,990,368 | B2 | 1/2006 | Simon et al. | 600/425 |
| 2002/0016544 | A1 | 2/2002 | Hareyama et al. | 600/411 |
| 2002/0057825 | A1 | 5/2002 | Evron et al. | 382/128 |
| 2003/0032866 | A1 | 2/2003 | Winter et al. | 600/300 |
| 2003/0199759 | A1 | 10/2003 | Richard | 600/426 |
| 2003/0215124 | A1* | 11/2003 | Li | 382/131 |
| 2004/0054248 | A1 | 3/2004 | Kimchy et al. | 600/3 |
| 2004/0102697 | A1 | 5/2004 | Evron | 600/424 |
| 2004/0136491 | A1 | 7/2004 | Iatrou et al. | 378/4 |
| 2005/0070821 | A1 | 3/2005 | Deal et al. | 600/585 |
| 2005/0101987 | A1 | 5/2005 | Salahich | 606/200 |
| 2005/0107688 | A1 | 5/2005 | Strommer | 600/424 |
| 2005/0113686 | A1 | 5/2005 | Peckham | 600/431 |
| 2006/0058647 | A1 | 3/2006 | Strommer et al. | 600/434 |

FOREIGN PATENT DOCUMENTS

| | | |
|---|---|---|
| EP | 1 005 835 A1 | 6/2000 |
| EP | 0 885 594 B1 | 4/2003 |
| RU | 2119765 C1 | 10/1988 |
| WO | WO 96/25881 A1 | 8/1996 |
| WO | WO 99/13432 A1 | 3/1999 |
| WO | WO 01/58359 A1 | 8/2001 |
| WO | WO 01/85030 A1 | 11/2001 |
| WO | WO 02/36013 A1 | 5/2002 |
| WO | WO 03/096884 A2 | 11/2003 |
| WO | WO 2005/008583 A2 | 1/2005 |
| WO | WO 2005/020148 A1 | 3/2005 |
| WO | WO 2005/031635 A1 | 4/2005 |
| WO | WO 2006/033113 A2 | 3/2006 |
| WO | WO 2006/061815 A1 | 6/2006 |

OTHER PUBLICATIONS

Russakoff D B et al "Intensity-based 2D-3D spine image registration incorporating a single fiducial marker" Academic Radiology, Reston, VA, US, vol. 12, No. 1. pp. 37-50, Jan. 2005.

Srihari R et al "Image background search: combining object detection techniques with content-based image retrieval (CBIR) systems" Content-Based Access of Image and Video Libraries, 1999. (CBAIVL '99). Proceedings. IEEE Workshop on Fort Collins, CO, US, Los Alamitos, CA, USA,IEEE Comput. Soc, US, 1999, pp. 97-101.

Eiho S et al "Preoperative and intraoperative image processing for assisting endovascular stent grafting" Informatics Research for Development of Knowledge Society Infrastructure 2004.ICKS 2004. International Conference on Kyoto, Japan Mar. 1-2, 2004, Piscataway, NJ, USA,IEEE. pp. 81-88.

Close R A et al "Accuracy Assessment of Layer Decomposition Using Simulated Angiographic Image Sequences" IEEE Transactions on Medical Imaging, IEEE Service Cente, Piscataway, NJ, US, vol. 20, No. 10. pp. 990-998, Oct. 2001.

Nelson T R et al "Three-dimensional ultrasound imaging" Ultrasound in Medicine and Biology, New York, NY, US, vol. 24, No. 9. pp. 1243-1270, 1998.

Bankman I "Handbook of Medical Imaging Progressing and Analysis" 2000, Academic Press, San Diego, London. pp. 359-374.

Garreau M et al. "A knowledge-based approach for 3-D reconstruction and labeling of vascular networks from biplane Angiographic projections" IEEE transactions on medical imaging, US, IEEE inc. vol. 10 , No. 2, Jun. 1991.

Automatic Segmentation of the Coronary Artery Tree in Angiographic Projects, by Marc, Schrijver and Cornelis H. Slump, published in Proceedings of ProRISC Nov. 28-29, 2002.

* cited by examiner

METHOD AND APPARATUS FOR GUIDING A DEVICE IN A TOTALLY OCCLUDED OR PARTLY OCCLUDED TUBULAR ORGAN

RELATED APPLICATIONS

The present invention is the national stage of International Application No. PCT/IL2006/01214, filed Oct. 22, 2006. The present invention relates to international patent application serial number PCT/IL2005/000360 titled METHOD AND APPARATUS FOR POSITIONING A DEVICE IN A TUBULAR ORGAN filed on filed Mar. 31, 2005. The present invention relates to international patent application serial number PCT/IL2005/001024 titled APPARATUS AND METHOD FOR FUSION AND IN-OPERATING-ROOM PRESENTATION OF VOLUMETRIC DATA AND 3-D ANGIOGRAPHIC DATA filed on Sep. 24, 2004, the contents of which are incorporated herein by reference.

BACKGROUND OF THE INVENTION

1. Field of the Invention

The present invention relates to medical systems in general, and to a method and apparatus for positioning and presenting a device in tubular organs, in particular.

2. Discussion of the Related Art

Interventional cardiology procedures are becoming increasingly important in the treatment of physiological abnormalities such as lumen stenosis or aneurysm. For example, in order to treat a stenotic coronary artery, it is often required to inflate a balloon, apply an artherctomy or thrombectomy device and place a stent (prosthesis) at a diseased artery site. In this example, the devices are either a guide wire or a therapeutic intravascular device, such as a balloon, a stent, an atherectomy, or a thrombectomy device. On the therapeutic stage of the catheterization procedure the physician inserts a guide wire, mounting it distally of the stenotic vessel and then delivers the therapeutic device (balloon or stent) to the stenotic location. In cases of cases of difficult morphology of the vessel the guide wire insertion becomes a challenging task even for skilled physicians. Furthermore, navigation of the guide-wire in anatomies such as bifurcations and branches is always a challenging task. In order to accurately locate the device within the artery, fluoroscopic x-ray images are taken during the navigation of the guide-wire into position. In addition, the subject is often injected with contrast material which facilitates the view of the arteries in the image as well. Real-time assistance in navigation and localization of the guide-wire could prove very helpful in such cases and may reduce contrast material injection.

Another situation where real-time assistance on navigation and localization of tools is required is a Chronic Total Occlusion (CTO) or near total occlusion. In a CTO or near total occlusion situation, the artery is totally occluded by sediments, meaning that neither blood nor contrast material can flow through the artery beyond the occlusion area, so the part of the artery beyond the occlusion area can not be imaged during the operation. Thus, when a physician wishes to insert a device such as a driller in order to open the occlusion, he lacks information about the morphology of the artery beyond the occlusion area. The lack of information can result in the physician drilling not along the morphology of the artery but in such an angle that the artery walls are damaged or even punctured. Puncturing, accompanied by the restored blood flow may expose the patient to a significant danger.

Accurate deployment of the therapeutic device is another important factor of therapy success. This is true for example, for stents and especially for drug-eluting stents, bi-ventricular pacing lead or the like. A capability of automatically and accurately locating a device with minimal injecting additional contrast materials, and without requiring additional equipment beyond the already used guide wire and device yield benefits. Thus, in the disclosed invention all involved tasks are carried out automatically without altering the standard flow of a catheterization procedure.

In the context of this invention, the term "device" refers interchangeably to a guide wire tip and to a therapeutic device as well as drilling device. When the tubular organ is an artery, the therapeutic device is an intravascular therapeutic device, such as a stent or a balloon. The location of a catheter tip, guide wire tip or intravascular therapeutic device with reference to surrounding arterial anatomy is monitored by X-ray fluoroscopy. When necessary, the angiographer releases a contrast material, such as iodine solution, from the catheter tip. The contrast material is carried from the catheter tip by the blood flow, and an X-ray image of the arterial anatomy in the vicinity of the catheter tip is obtained, showing both the artery and the catheter tip. Based upon the obtained X-ray image, the guide wire is advanced until the desired arterial anatomy is reached. Usually, in order to treat the artery, the tip of the guide wire should pass through the diseased region to the distal end of the diseased region. Subsequently, an intravascular device is mounted on the guide wire and brought to the diseased arterial region. Monitoring the location of the therapeutic device inside the artery is performed by following the movement of radio-opaque markers sliding along the guide wire that flanks the device. The markers indicate the position of the device in reference to the guide wire.

Most of the known navigation methods use special equipment for therapeutic device localization. Such equipment can be based on optical or electro magnetic tracking principles using sensors and transducers for measuring position of the device in some reference coordinate system. In order to achieve acceptable results the imaging system and the tracking systems must be well calibrated presenting the image and location of the device in common coordinate system. Additional equipment increases the cost of procedure, makes it more complicated, and requires accurate calibration. Another type of methods for device positioning uses mechanical tools which confine the right positioning for the device. These methods serve specific types of treatments and therefore are not universal. International patent application publication number WO 96/25881 titled METHOD FOR ULTRASOUND GUIDANCE DURING CLINICAL PROCEDURES published on Aug. 29, 1996 describes a method for combining a geometric localization of a tool with acquired ultrasound images. However, ultrasound modality cannot be applied for some organs, such as coronary arteries. WO 96/25881 further describes a method for guiding a tool to reach an organ without intersecting other organs. WO 96/25881 does not relate to navigating a tool located inside a tubular organ towards a pre-defined position within the tubular organ. The target and surrounding organs are required to be visible in images acquired throughout the insertion. Thus, the main difficulty of the registration, which is an essential step in data fusion, is solved by using additional equipment— the organs are imaged by ultrasound throughout the insertion. The last solution is not valid for the case of X-ray angiography, for example.

Another publication demonstrating the usage of Ultrasound technology for real-time imaging of devices, is International patent application publication number WO 01/58359 titled ULTRASONIC IMAGER published on Aug. 16, 2001. WO 01/58359 discloses an ultrasound imaging system that superimposes sectional views created from volumetric ultrasound data, and the location data for an intervention device, such as a catheter as obtained from external sensors. The position of an interventional medical device may be shown, in one or more views, relative to organs and tissues within a body as the interventional device is moved. The interventional device positional data is updated continuously and is superimposed on tissue images that may be updated less frequently, resulting in real-time or near real-time images of the interventional device relative to the tissues. The superimposed images permits medical personnel to perform procedures such as angiograms with minimal or no exposure of patients to x-rays and contrasting dye. The current ultrasound image where catheter appearance is enhanced by vibration mechanism or by brightening technique is supposed to be aligned with a reference image. The combination of the two images is carried out by straightforward overlay. However, as mentioned above, ultrasound technology is not applicable to all organs, and especially to coronary arteries, since the technology does not compensate for changes in imaging conditions and for movement of organs.

U.S. Pat. No. 6,389,104 entitled FLUOROSCOPY BASED 3-D NEURAL NAVIGATION BASED ON 3-D ANGIOGRAPHY RECONSTRUCTION DATA discloses a method for detection of a moving catheter in a lower quality fluoroscopic image and presenting the catheter with high quality 3D reconstructed vascular vascular structure. The suggested method assumes complete information of the imaging perspective geometry both on the diagnostic stage when the 3D model is generated by using images captured by a rotational angiography and on the therapeutic stage of fluoroscopy guided navigation of catheter. Under such restrictive and practically problematic assumptions, one of the central problems of image registration is reduced to essentially carrying out known transformations. Additionally, the suggested method is not applicable to moving organs, such as arteries whose shape changes with the heart beat cycle. Yet another drawback of the method is that the catheter is identified in low quality fluoroscopic images by usage of special intensity modulated catheter. Thus, the method requires complete information of the imaging conditions, a static scene and a special catheter, making it inapplicable for standard coronary angioplasty.

There is therefore a need in the art for a system that will generate a model of a body area including tubular organs, during a diagnostic stage, and will use the generated model for purposes of automatic identification and tracking of a device located inside a tubular organ during a therapeutic stage. It is desirable that the system will use x-ray imaging during the therapeutic stage, although most tubular organs, such as vessels are not visible in x-ray images. The system should not require additional equipment in excess of the equipment currently required for the relevant types of procedures. It is also desirable that the system will perform automatic registration of images between images captured during a diagnostic step and images captured during a therapeutic stage overcoming geometric distortions and differences in content. The system should automatically register the images, determine the location of the device, and will display the device, along with relevant measurement data, together with reference images of the body area or the reconstructed model thereof. The system should minimize the need for harmful contrast material injections and radiations to the subject.

SUMMARY OF THE PRESENT INVENTION

The present invention provides a novel method and apparatus for navigating a device through an occluded section of a tubular organ, such as in chronic total occlusion or chronic near-total occlusion situations.

In accordance with a preferred embodiment of the disclosed invention there is thus provided a method for displaying an image of a device within an occluded tubular organ of a subject, for assisting in navigating the device through an occluded area of the tubular organ, the image representing the device, the occluded area of the tubular organ, a part of the tubular organ proximal to the occluded area a, and a part of the tubular organ distal to the occluded area, the method comprising: registering a current image taken by an imaging modality showing at least two points of the device, with a last injection image, the last injection image imaging a part of the tubular organ proximal to the occluded area, and an area immediately distal to the occluded area appearing insufficiently distinguishable from background; registering the last injection image with a reference image showing the occluded area, a part of the tubular organ proximal to the occluded area, and a part of the tubular organ distal to the occluded area; fusing information from the current image, the last injection image and the reference image, to obtain a displayed image comprising the device, the occluded area of the tubular organ, a part proximal to the occluded area of the tubular organ, and a part distal to the occluded area of the tubular organ. The reference image is optionally constructed from a reference source, the reference source constructed from images taken by a second imaging modality. The method can further comprise a step of navigating the device along the tubular organ using the combined image to penetrate the occluded area. The imaging modality is optionally an angiogram, and the second imaging modality is optionally a Computerized Tomography imaging device. The method can further comprise the steps of: receiving at least two images of at least two cross sections of the tubular organ; determining a penetration area; and penetrating the occluded area at the penetration area. The cross sections are optionally constructed from the reference source. The method is optionally used for chronic total occlusion or for chronic near total occlusion.

Another aspect of the disclosed invention relates to an apparatus for aiding the navigation of a device within a an occluded tubular organ of a subject, the apparatus comprising: a detection component for detecting on an image the device within the tubular organ of the subject; a registration component for: registering a current image taken by an imaging modality showing at least two points of the device, with a last injection image, the last injection image imaging a part of the tubular organ proximal to the occluded area, and an area immediately distal to the occluded area appearing insufficiently distinguishable from background; and registering the last injection image with a reference image showing the occluded area, a part of the tubular organ proximal to the occluded area, and a part of the tubular organ distal to the occluded area; and a display preparation component for rendering a combined image showing the device, the occluded area of the tubular organ, a one part of the tubular organ proximal to the occluded area and a part of the tubular organ distal to the occluded area. The tubular organ is optionally an artery suffering from chronic total occlusion or from chronic near total occlusion. The apparatus can further comprise an automatic navigation system for automatically navigating the device within the tubular organ through the occluded area.

Yet another aspect of the disclosed invention relates to a computer readable storage medium containing a set of instructions for a general purpose computer, the set of instructions comprising: registering a current image taken by an imaging modality showing at least two points of a device, with a last injection image, the last injection image imaging a part of a tubular organ proximal to an occluded area of the tubular organ, and an area immediately distal to the occluded area appearing insufficiently distinguishable from background; registering the last injection image with a reference image showing the occluded area, a part of the tubular organ proximal to the occluded area, and a part of the tubular organ distal to the occluded area; fusing information from the current image, the last injection image and the reference image, to obtain a displayed image comprising the device, the occluded area of the tubular organ, a part proximal to the occluded area of the tubular organ, and a part distal to the occluded area of the tubular organ.

BRIEF DESCRIPTION OF THE DRAWINGS

The present invention will be understood and appreciated more fully from the following detailed description taken in conjunction with the drawings in which.

DETAILED DESCRIPTION OF THE PREFERRED EMBODIMENT

Figure 1:
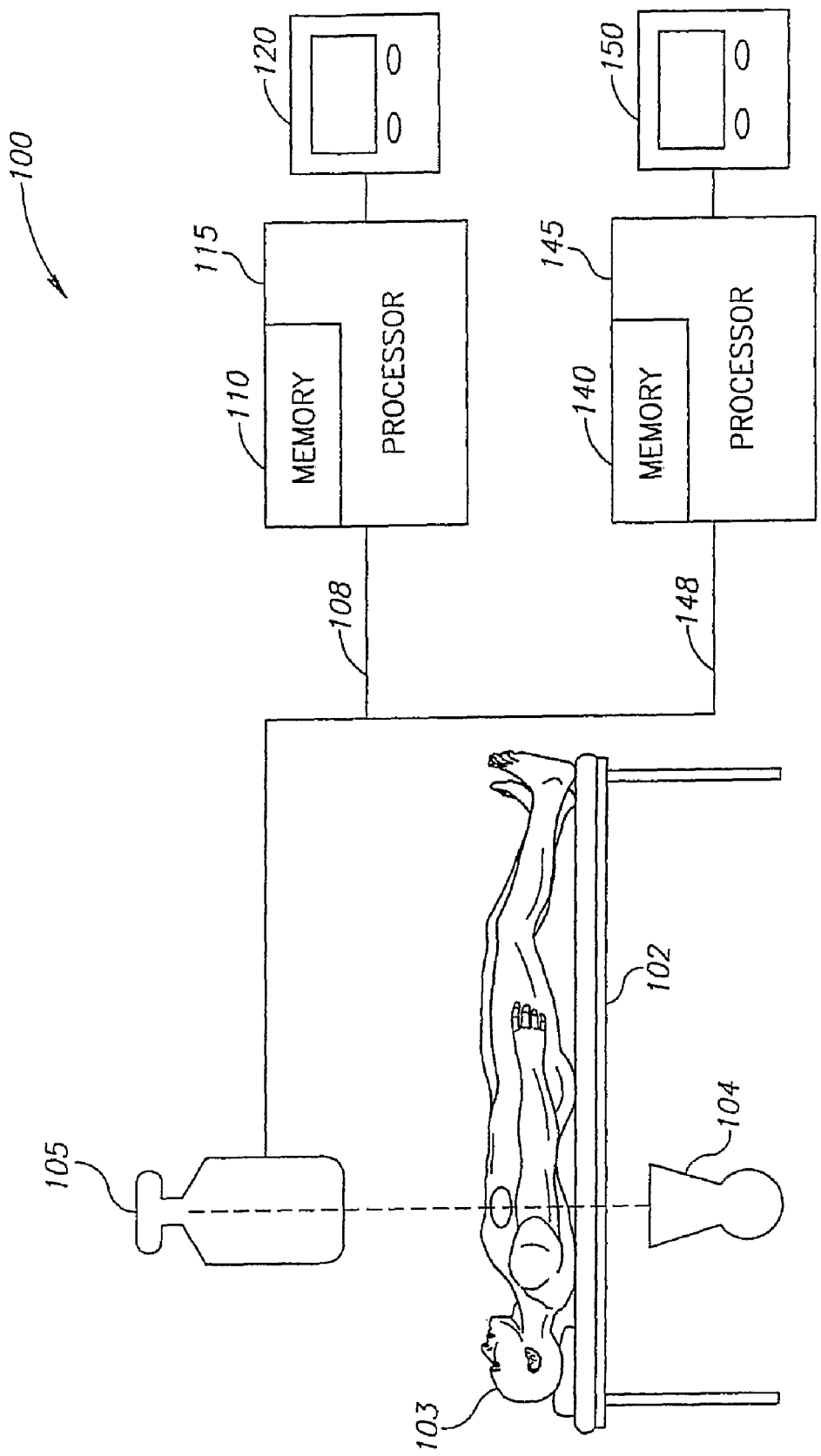
FIG. 1 is an illustration of a typical environment in which the proposed invention is used.

The disclosed invention presents an apparatus and method for automatic detecting and tracking of a device within a tubular organ, such as an artery, a blood vessel, or a urethra of a subject. In the context of the disclosed invention, "device" relates either to a guide wire tip, a catheter tip, or any other therapeutic device, such as driller. When the tubular organ under discussion is an artery, the therapeutic device is usually an intravascular therapeutic device, such as a stent, a balloon, a pacing lead, or the like.

The present invention can be implemented, but is not restricted to in the following procedures: catheterization procedure, bi-ventricular pacing, coronary angiography, coronary angioplasty, peripheral angiography, peripheral angioplasty, carotid angiography, carotid angioplasty, neuro angiography/plasty, biliary imaging or intervention, and the like.

In a preferred embodiment, the method of the present invention employs a diagnostic stage and a therapeutic stage. During the diagnostic stage, a 2-dimensional or 3-dimensional model of the relevant body area, including the tubular organs is constructed from images of the subject. The 2-dimensional or 3-dimensional images are acquired by an x-ray machine, Computerized Tomography (CT), or any other like modality. In a preferred embodiment of the disclosed invention, in addition to constructing a model of the body area, a suitable therapeutic device and location for the therapeutic device within the tubular organ are determined and marked during the diagnostic stage. The therapeutic device type and location are determined in order to provide the patient with appropriate treatment, taking into consideration the morphology and the dimensions of the diseased area. Additionally, the system marks preferred C-arm perspectives to be employed during the insertion of the device. In an alternative embodiment, the system uses a model received from an external source rather than generating the model. In another preferred embodiment, the system determines a feedback control for a system that automatically controls the advancement or the shape of the device at a therapeutic stage.

In another preferred embodiment, the method employs a therapeutic stage only, during which the system uses the model received or generated during the diagnostic stage, together with current x-ray images taken during the therapeutic stage to locate, track and display a device inside the tubular organ. During a typical therapeutic stage, a guide wire having a tip is navigated to the required area of the body. Then a therapeutic device is mounted on the guide wire and led to a required location by sliding along the guide wire. The device is located and tracked by following the movement of radio-opaque markers located thereon, in a series of current x-ray images. In an alternative embodiment, the markers are not opaque but are otherwise visible using alternative means or modalities. Then, the current images and a 2-dimensional projection of the model, employing substantially the same projection angle and parameters as the current images, are superimposed thus showing simultaneously the device and the region of the artery. The device is advanced in the artery towards the desired region, based upon a comparison of the present location of the device in the artery and the desired location, if marked. This process is repeated until the device appears in an image in the region of the artery where the operator determined it should be located. When necessary, contrast material is released from the catheter tip and a current image showing the artery and the device is obtained.

The main difficulty in locating and displaying the device as captured in the current image in conjunction with the model, is that the two sources of information, i.e., the model and the current image are different both in content and in geometry. In order to fuse and present contents from multiple sources on one image, the sources should be registered with each other, i.e. be translated into a common coordinate system. The common coordinate system can be the coordinate system of one of the sources, translating the coordinate systems of the other sources, or a different coordinate system, in which case all sources should be translated to the common coordinate system.

The difference in content stems from the reference model containing organs only, since the device was not present at the time the model was generated, and the current images mostly containing the device only. The current images mostly contain the device only, since tubular organs are shown only on images taken after injecting the subject with contrast material. The differences in the geometry stem both from the different imaging characteristics, such as C-arm positions, intensity, and the like, and the difference in the shape of the tubular organs caused by the presence of the device therein. In a preferred embodiment this twofold gap is bridged by using a mediating image, captured during the therapeutic stage with contrast material injection, hereby referred to as last injection image. This mediating image has common content with the model, since it shows the tubular organs. In particular, it has common content with the images participating in the construction of the model, or with an appropriate 2-dimensional projection of the model. On the other hand the mediating image has imaging conditions which are similar to those of the current image, although the content is generally different due to the absence of the tubular organs in the current image. Thus, the presented method preferably involves a two-stage registration process—from the current image to the mediating image, and from the mediating image to a reference image participating on the model or a projection thereof.

Referring first to FIG. 1, showing a preferred embodiment in which the present invention is used, generally referenced as 100. System 100 is used for positioning a catheter or intravascular device at a desired location within an artery in accordance with one exemplary embodiment of the invention. The system comprises a table 102 upon which a patient 103 lies. An X-ray source 104 is located under table 102 for projecting X-rays through patient 103 to an X-rays camera 105 located above table 102, diametrically opposite X-ray source 104. X-ray camera 105 generates video signals or digital images 108, for example in DICOM format representing one or more X-ray images of patient 103. Video signals or digital images 108 are stored in a memory 110 of a processor 115. Images captured by X-ray camera 105 may be viewed on a display device 120, such as a monitor or any other display device, either in real-time or after being retrieved from the memory 110. The images can be captured either at a diagnostic stage, or at a therapeutic stage, or both. In an alternative embodiment, the x-ray source and camera can be placed in other locations. In yet another alternative, the imaging equipment can be another modality, such as Computerized Tomography, Magnetic Resonance, or the like. Processor 115 is preferably a computing platform, such as a personal computer, a mainframe computer, or any other type of computing platform that is provisioned with a memory device 110, a CPU or microprocessor device, and several I/O ports (not shown). Alternatively, processor 115 can be a DSP chip, an ASIC device storing the commands and data necessary to execute the methods of the present invention, or the like. Processor 115 can further include a storage device (not shown), storing the device guidance application. The device guidance application is a set of logically inter-related computer programs and associated data structures that interact to detect and track a device in an x-ray sequence, and register the frames with a pre-acquired 3-dimensional model of the relevant body area. The device guidance application is detailed in association with FIG. 4 below. The computerized steps of the proposed method can be implemented on processor 115 and the output displayed on display device 120. Alternatively, the computerized steps of the proposed method can be implemented on a dedicated processor 140, receiving video signals or digital data 148 from X-ray camera 105, and comprising a memory device 145. The output of the method can be displayed on a dedicated display 150.

Figure 2:
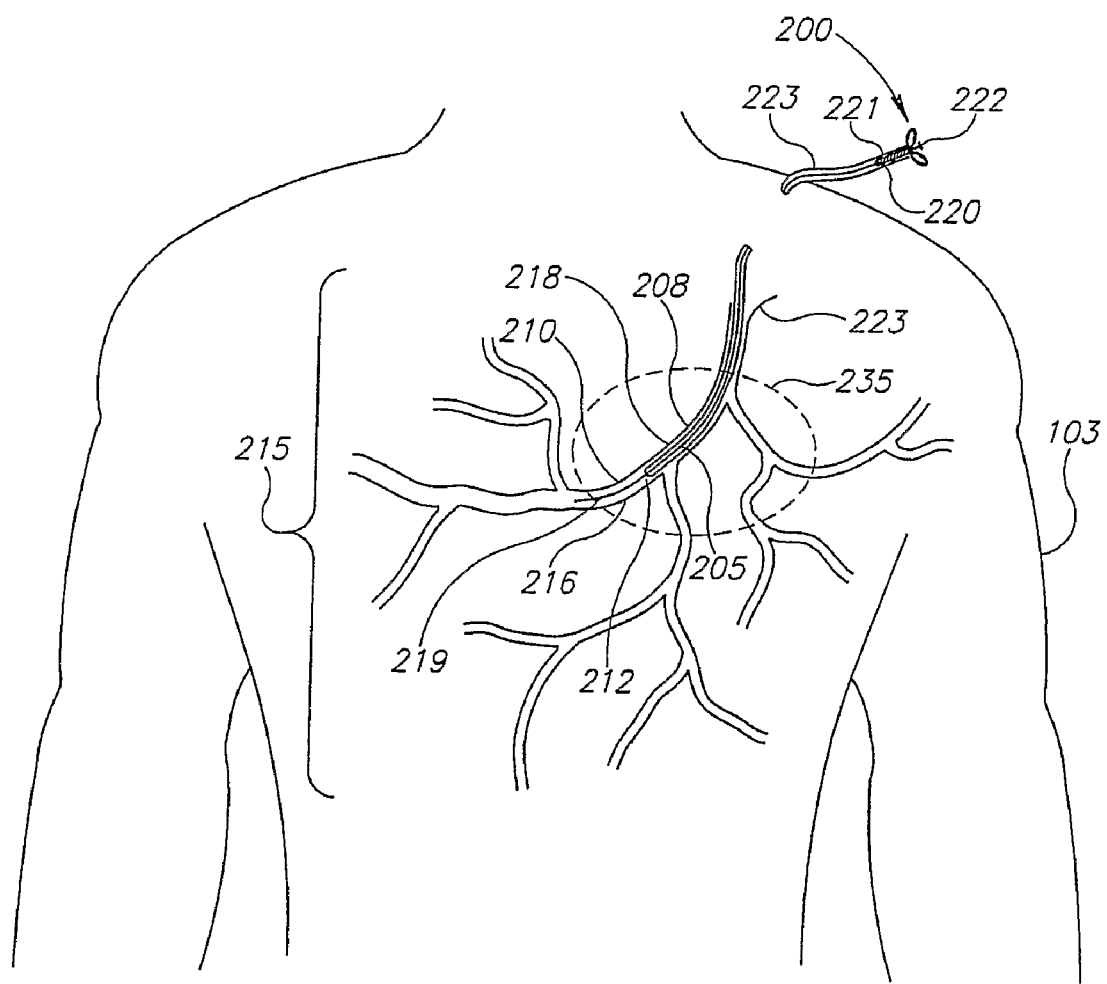
FIG. 2 is an illustration of a device being navigated through an arterial system, in accordance with a preferred embodiment of the present invention.

Referring now to FIG. 2, showing a catheter 200, having a tip 205 positioned at an aperture 212 of an artery 210 that is a part of an arterial tree 215 of patient 103. Catheter 200 may be used to deliver an intravascular device 218 mounted on a guide wire 216 to a desired location 219 within artery 210. Catheter 200 is connected to a reservoir 220 containing a radio-opaque liquid 221 such as an iodine solution that is conducted from reservoir 220 to catheter tip 205 and released from catheter tip 205 as required by depressing a piston 222. When contrast material 221 is released from catheter tip 205, an image is obtained of the arterial tree in area 235 around catheter tip 205 by X-ray camera 105. Based upon the obtained image, catheter tip 205 is brought to arterial system 215, which contains artery to be treated 210. Then, guide wire 216 is extended from catheter tip 205 and brought to the diseased region within an artery 219 using fluoroscopy and short injections of contrast material. After positioning of guide wire 216 within artery 210, a device 218 is inserted into artery 210 towards region to be treated 219 along guide wire 216.

Figure 3:
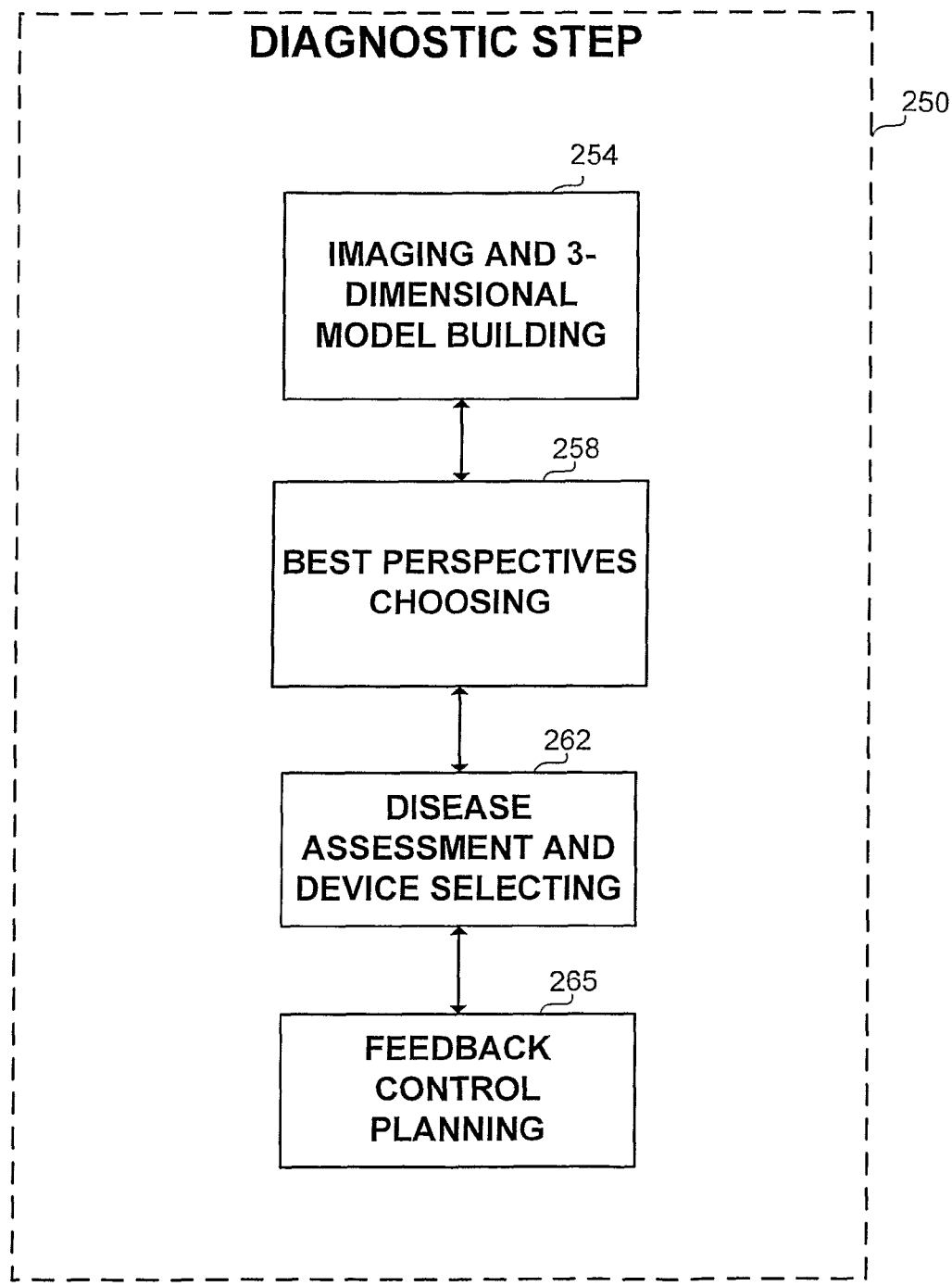
FIG. 3 is a block diagram describing the operational steps associated with a diagnostic step, in accordance with a preferred embodiment of the present invention.

The method of the present invention involves two groups of steps, a diagnostic step group and a therapeutic step group. Referring now to FIG. 3, showing a flowchart of the diagnostic step group, generally referenced as 250, in accordance with the method of the present invention. Step group 250 comprises step 254, in which the vessels are imaged with a C-arm X-ray angiographer from different perspectives, and a 3-dimensional reconstruction of the tubular organ is built using two or more 2-dimensional images. The process of reconstruction includes analysis of the vessel tree surrounding the stenosis and calculation of relevant information, for example vessel centerline, boundaries, diameters and so on. This step is further disclosed in Applicant's International patent application publication number WO 01/85030 titled SYSTEM AND METHOD FOR THREE-DIMENSIONAL RECONSTRUCTION OF AN ARTERY published on Nov. 15, 2001. Then, at step 258 the best perspectives for viewing the artery during a catheterization are determined. The perspectives comprise the position of the C-arm which will yield the best view of the artery. At step 262, based on the reconstruction and associated measurement data, the physician assesses the severity of the disease and select the most appropriate type of therapeutic device. The system can offer, given enough device information, a default location for the device deployment, though the physician can interactively choose a desired location for the device. At step 265, additional information, useful for the navigation of the device along the artery, for example landmarks, such as branching points or points with maximal curvature, or rules determining a feedback control for advancement and deployment of the device is also provided. This information includes also a complexity index comprising local curvatures, tortuosity, and locally preferable C-arm orientation for navigation, i.e. projection minimizing local foreshortening. Preferable C-arm orientation can be selected from the perspectives used during the 3D reconstruction or as overall optimal orientation. Step 254 is performed first, and steps 258, 262, 265 are performed following step 254, in any required order, or simultaneously.

In an alternative embodiment, the model building step is skipped, and the 3-dimensional model of the artery is acquired from an external source, and the perspectives determination and device selection steps are skipped. In a yet another alternative, the steps of the perspectives determination and device selection are performed on a 3-dimensional model of the artery as received from an external source.

Figure 4:
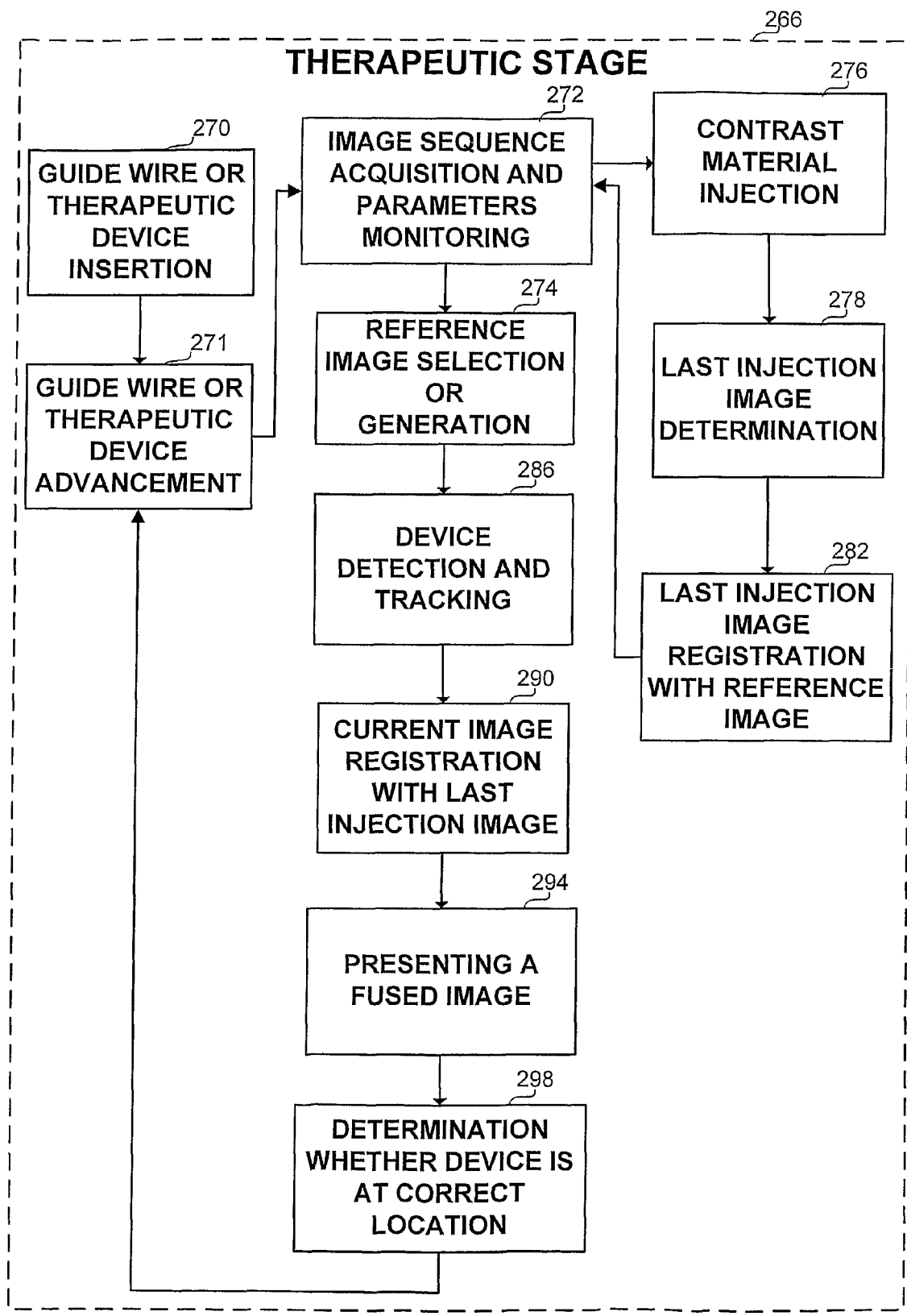
FIG. 4 is a block diagram describing the operational steps associated with a therapeutic step, in accordance with a preferred embodiment of the present invention.

Referring now to FIG. 4, showing a flowchart of the therapeutic group of steps, generally referenced as 266, in accordance with the method of the present invention. Therapeutic step group 266 is employed during a catheterization or another operation, such as an intravascular operation. Step group 266 comprises step 270, in which a guide wire is introduced to the artery so that its tip is placed distally to the diseased vessel segment. A therapeutic device is preferably mounted on the guide wire and advanced along the wire to the required location. The therapeutic device is usually a balloon or a balloon and a stent, sliding along the guide wire. When the balloon or the stent or both reach the designated position it is inflated or deployed. At step 271, the guide wire or the device is advanced within the tubular organ towards the required location. At step 272 the system monitors in real-time the acquisition of cine/fluoroscopic sequences, the C-arm parameters and ECG signal. The ECG signal serves as a tool for gating, i.e. choosing an image frame from the video stream being in the same phase of the heart beat cycle as the reference image. The gated frame is the highest correlated frame with the reference image. If the required update rate is higher than once every heart beat, the relevant images are assigned with a synchronization tag. If an ECG signal is not available, the synchronization parameter can be deduced based on correlation criteria between the captured images and the reference images. At step 274, a reference image is selected or generated. If the current C-arm orientation is close to the orientation of one of the images that participated in the 3-dimensional model reconstruction, this image is selected by the system as a reference image. If no such image exists, a synthetic reference image is constructed by means of projecting the 3-dimensional model to the imaging plane of the current C-arm orientation. At step 276, which is optional and occurs according to the physician's discretion, the subject is injected with contrast material, and at step 278, contrast material injected images are determined, requiring that all acquired sequences preferably go through analysis of the iodine injection. For example, each frame in each sequence passes a preprocessing enhancing the vessels, and receives a score indicating the presence of vessel-like features. Analyzing the scores as a function of time, the method identifies iodine injection sequences. Using the ECG signal monitored at step 272, a frame synchronized with the reference frame is chosen. The chosen frame serves as a last injection image for the current C-arm orientation. When an ECG signal is not available, the last injection frame is determined using, for example, a correlation criterion between each frame and the reference image. The last injection image for every C-arm orientation used in the navigation process is stored in the memory and is retrieved when C-arm returns to the orientation previously used in the navigation process. Step 278 is performed in accordance with step 272 at which the sequences are captured. At step 282, the last injection image is registered with the reference image. This is facilitated by the contrast material showing the arteries. Steps 278 and 282 do not require real time implementation. Rather, they could be performed in near real time. Upon completion of step 282 the previous last injection image is substituted with the new one.

At the beginning of the navigation, a last injection image does not exist yet. Sometimes, the last injection image is not available for the whole procedure. Therefore, the current image is registered directly with the reference image. At step 286, the device, i.e., the guide wire tip or the markers on a therapeutic device is detected and tracked in real-time on the current image. The detection and tracking is different for a guide wire tip and for a therapeutic device. The processes for the detection and tracking are detailed below. At step 290, the current image is registered with the last injection image, or directly with the reference image. This step is also further detailed below. At step 294, the guide wire tip or the device, whose location was found at step 286 are fused and presented together with the reference image, on a combined image, thus providing a fused image of the artery, its surroundings and the device therein. The fused image is displayed on display device 120 if FIG. 1. Steps 290 and 294 are also performed in real-time, for each captured image. The fused presentation reduces the need for contrast material injections and provides assistance for accurate device deployment. At step 298, the system determines and presents the distance between the device and the designated location, as marked during the diagnostic stage, or the distance between the device and a known landmark designated during the diagnostic stage, such as a bifurcation point, maximal curvature point, or the like. In a preferred embodiment, the determined location of the device is sent as input to a feedback control system which automatically controls the advancement or the shape of the device. Steps 271, 272, 274, 286, 290, 294 and 298 are repeated until the physician determines that the device is properly located, and at a higher rate than steps 276, 278, and 282, which are performed according to the physician's discretion.

Optionally, the 3-dimentional model building is skipped, which requires the therapeutic step group to employ a 3-dimensional model received from an external source. In a case, if the best perspectives and device selection steps are skipped, the determination of the distance between the location of the device and its designated location is skipped as well.

Figure 5:
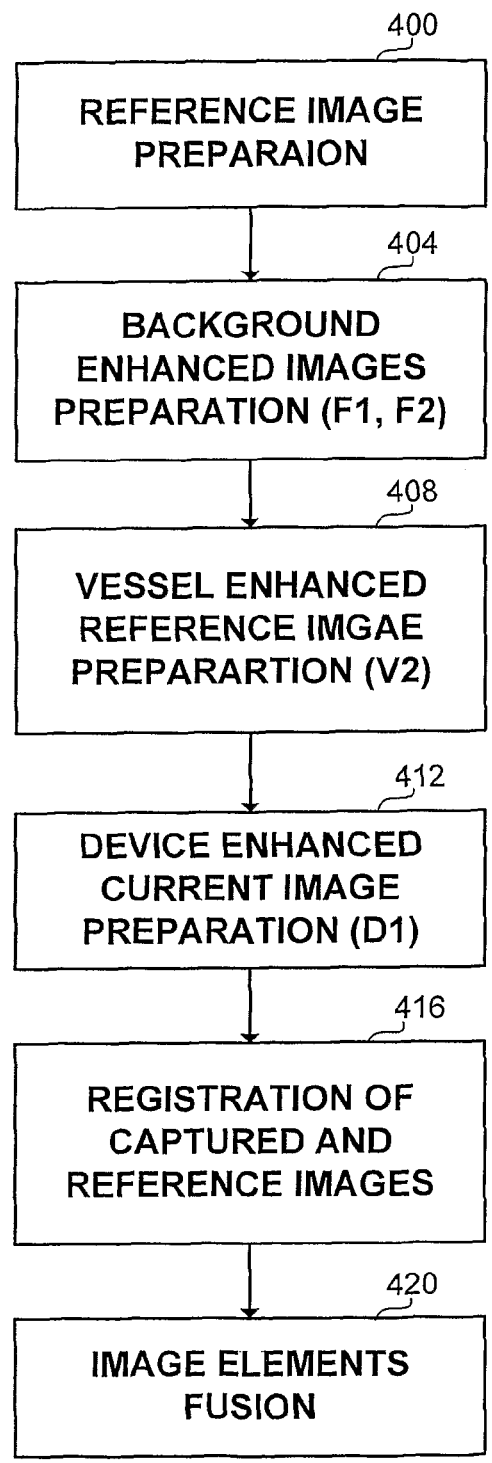
FIG. 5 is a flowchart of the registration method, in accordance with a preferred embodiment of the present invention.

Referring now to FIG. 5, describing in detail the registration task which is also integrated with the identification and tracking tasks of the method and apparatus. The registration presented in FIG. 5 is applicable when directly registering a current image to the reference image representing a reference source, or when incorporating a last injection image as a mediating image. In the latter case, two registrations are performed: between the last injection image and the current image, and between the reference image and the last injection image. Each registration is preferably implemented according to the FIG. 5. The registration scheme utilizes the principle of constrained correlation. Constrained correlation of two images I1 and I2 means applying a requirement for markers detected in the current image to be translated to a vessel in the reference image or in the last injection image, since the markers are attached to a device which is known to be inside a vessel. Similarly, registering the reference image with the last injection image an additional constraint requires a traced artery segment in the reference image to be translated to a vessel in the last injection image. Generally, constrained correlation involves the construction of a combined correlation surface from two correlation surfaces $$CC(I1,I2)=f(C(F1,F2),C(D1,V2))$$

This definition implies that a combined correlation surface $CC(I1,I2)$ between images I1 and I2 is a result of the combination of two correlation surfaces: $C(F1,F2)$ and $C(D1,V2)$, where F1 and F2 are consistent features existing in the background of images I1 and I2, and therefore $C(F1,F2)$ expresses the correlation between the background features, D1 is a device enhanced image and V2 is a vessel enhanced image. For a non-limiting example, the correlation surface combination might be an element-by-element multiplication of the two correlation matrices $CC(I1,I2)=C(F1,F2) \cdot C(D1,V2)$ Another example for the function $f$ combining the two correlation surfaces is a product of the first correlation matrix $C(F1,F2)$ with a binarized version of the second correlation surface:

$CC(I1,12)=C(F1,F2) \cdot (C(D1,V2) > T)$. For clarity sake, the constrained correlation matrix between two images I1 and I2 is equal to the values of those pixels in the correlation matrix between the background features present in both images, for which the corresponding pixels in the correlation matrix between D1 and V2 exceed a certain threshold. The pixels in the constrained correlation score matrix, for which the correlation between D1 and V2 is below the threshold, are zeroed. For different registration tasks, involved with the navigation process, the images participating in the constrained correlation calculation can obtain specific forms, enhancing specific features.

FIG. 5 shows an exemplary registration task, performed as a stand-alone task of registering a single current image with a reference source. The reference source comprises a 2-dimensional or a 3-dimensional model of the body part, and the images used to construct the model. Unless otherwise mentioned, the method refers both to guide wire and to a therapeutic device. At step 400, a reference image is prepared out of the reference source, such as a model. The reference image I2 is, for example one of the images used to construct the reference model, or a projection of the model on the same plane as the current image. Then, at step 404, background enhanced images are prepared from the current image and form the reference image. The background enhanced images F1,F2 comprise consistent background elements captured in the two images, such as for example bones, or even the vessels (when the registration is between the reference image and the last injection image, which is not the case in the current example, and mentioned for the completeness of the description). The elements of the background are preferably enhanced using a gradient magnitude operator. Alternatively, the feature enhanced images are gradient vector field images, or Laplacian of Gaussian filtered images. At step 408 a vessel enhanced reference image V2 is prepared from the reference image. The vessel enhanced reference image is generated using a vessel resemblance operator. An improved vessel resemblance operator is detailed further below. At step 412 a specific device enhanced current image D1 is prepared from the current image I1. In the case of guide wire navigation a special filter is preferably applied for enhancement of thin dark lines. In the case of device navigation, the device enhanced image can be obtained by a dot-enhancing filter. When guide wire or device markers have been detected, image D1 can be constructed as a binary image depicting the found device. The generation of the binary image is further detailed in association with FIG. 6 below. At step 416, the registration itself between the current image I1 and the reference image I2 is performed using an implementation of the constrained correlation principle. In the case of direct registration of the current image with the reference image, the current image is preferably enhanced by explicit incorporation of the vessel model into it.

Registration between the current image and the last injection image is essentially similar to the registration between the current image and the reference image. At this step the registration between the reference image and the last injection image is already performed and the last injection image is preferably augmented by incorporating therein the vessel model translated from the reference image.

In the case of registration between the reference image and the last injection image, the reference image plays the role of I1 and the last injection image plays the role of I2. The feature images F1,F2 as well as image V2 are the vessel enhanced images (for example by vessel resemblance operator). The image D1 might be a binary image, representing the 2D model or projection of 3D model.

The registration of the last injection image and the reference image for therapeutic device navigation (such as a balloon or a stent) possesses some specific aspects. The difficulty of registration between last injection image and reference image results from changes in the imaging conditions, as well as changes in the shape of artery caused by the guide wire insertion and other changes between the diagnostic and the navigation stages. The preferred registration scheme adopts a multi level iterative approach of coarse to fine, global to local registration, including a method of constrained correlation achieving accurate result even under condition of severe distortions between the images. The registration process utilizes a multi resolution pyramid representation of the reference and the last injection images, and the application of feature enhancing filtering, such as vessel resemblance map generation for different resolution levels. The registration starts with constrained correlation on coarse pyramidal level, covering a larger area. Then a fine registration is carried out using repeating correlations in the smaller neighborhood of the stenosis region, for higher resolution levels and smaller correlation correlation windows. The process preferably uses correlation windows centered at the stenosis point, or multiple series of correlation windows centered along the reference artery centerline. Another variant of the fine registration is to use a process of automatic identification of the vessel segment in the last injection image, using the coarse registration and the known reference vessel segment. The process yields calculation of centerline and diameter of the vessel along the centerline, on the last injection image. Then the correlation between two one-dimensional diameter functions, one function relating to the last injection image and the other relating to the reference image is determined. The correlation can then be used for matching the centerlines and establishing local transformation between the images. At step 420, elements from both images are fused into one image.

Figure 6:
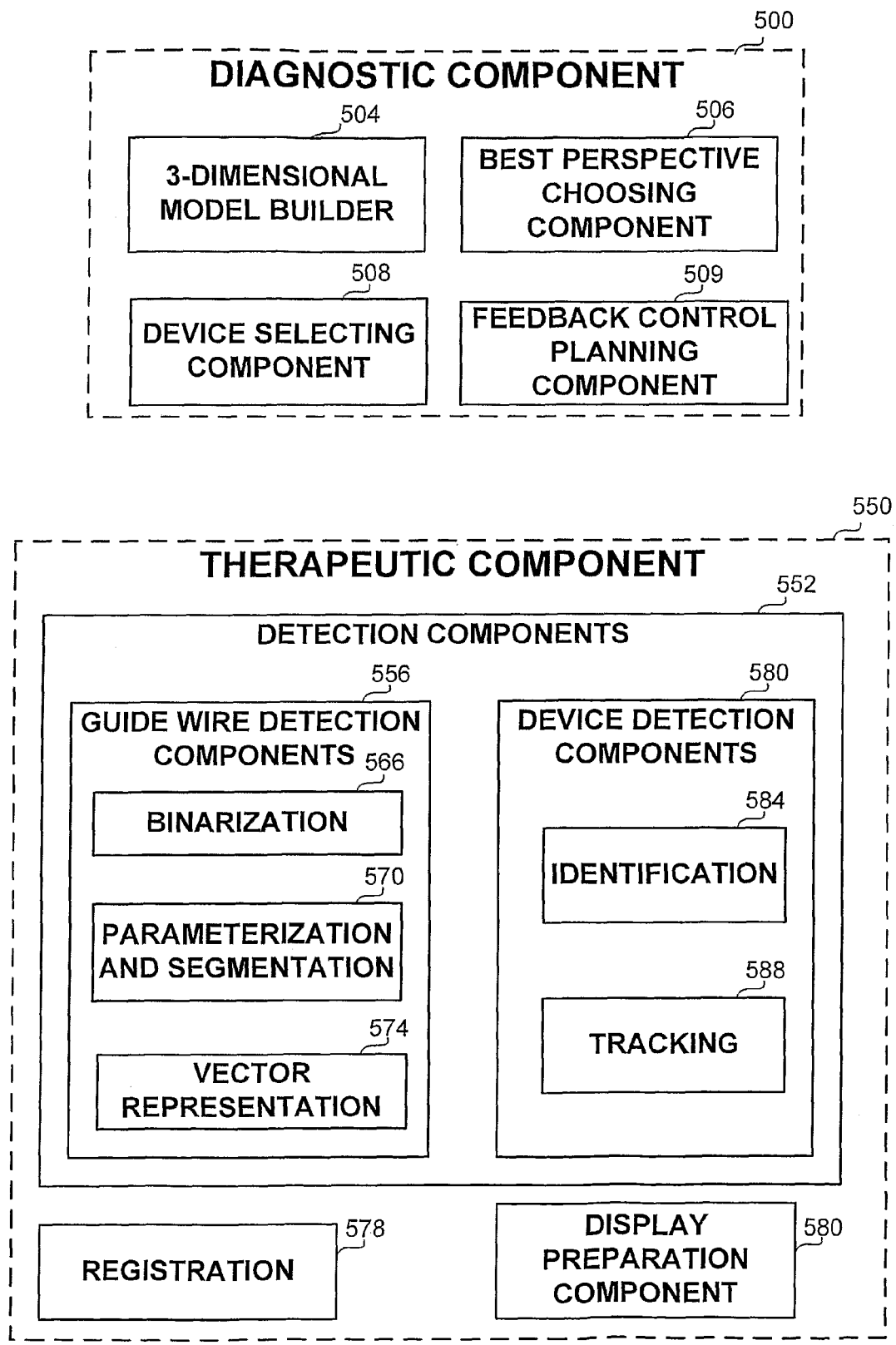
FIG. 6 is a block diagram of the components of the application, in accordance with a preferred embodiment of the present invention.

Referring now to FIG. 6, depicting the operating components of the guide wire and device guidance application which is a preferred embodiment of this invention. A diagnostic stage component 500 is responsible for processing the images acquired during a diagnostic and disease assessment stage.

Diagnostic stage component 500 comprises a 3-dimensional model builder 504, a best perspective choosing component 506, a device selection component 508, and a feedback control planning component 509. The tasks of component 500 and its sub-components are achieved by steps 254, 258 of the method presented in association with FIG. 3 above. Alternatively, component 504 can be omitted, provided the 3-dimensional model is obtained from an external source. A therapeutic stage component 550 comprises detection component 552, registration component 578 and display preparation component 580 for preparing the fused image comprising components from the registered images and rendering the fused or combined image. The operation of registration component 578 is detailed in association with FIG. 5 above. Detection components 552 comprise guide wire detection components 556 related to guide wire detection and device detection components 580, handling tasks related to a therapeutic device detection. Device detection components 580 further comprise identification component 584 and tracking component 588. The detection components are being activated according to the used equipment. Guide wire detection component 556 and registration component 578 are preferably implemented as a hybrid process, where registration component 578 is being activated between the activations of different components of detection component 556, but for clarity purposes the components are described separately. When detecting a guide wire, guide wire detection components 556 are being activated. Guide wire detection components 556 comprise a binarization component 566, which is responsible for performing binarization over the current image. Binarization is assigning a value of 1 to all pixels in the picture which have a value exceeding a predetermined threshold, and assigning a value of 0 to all other pixels. Preferably, the binarization is performed on the current image after a fast preprocessing for enhancing the guide wire tip. Normally, as a result of the binarization, one or a few clusters relating to the guide wire tip are distinguished, together with a number of small additional clusters spread over the image. Using the obtained binary image, a coarse registration to the last injection or reference image is performed, using registration component 578. Since the guide wire is known to be located inside a tubular organ such as a vessel, the registration can be performed, for example, by correlation of the guide wire tip segments with a vessel enhanced last injection or reference image or a corresponding binary image presenting the vessel relevant segment. As a result of the coarse registration, a translation of the current image to the reference image is obtained.

Parameterization and segmentation component 570 performs a parameterization of the pixels relatively to the centerline of the artery segment. The centerline of the artery segment is a part of the model of the body part built during the diagnostic step, or received from an external source. Specifically, each pixel in the reference image is assigned two parameters: The first parameter is the shortest distance between the pixel and the centerline of the artery. The second parameter is the index of the pixel in the centerline which is the closest to the pixel under discussion. Since the centerline is indeed a line, its pixels can be ordered and indexed. The parameterization calculations can be carried out on the diagnostic stage or once a synthetic reference image is created. Using the translation between the reference image and the current image found by the coarse registration, the parameters are assigned to the pixels having a value of 1 in the binarized current image. Then, the pixels in the current image are sorted according to the index of the nearest pixel in the centerline and can be presented and treated as a one-dimensional function of the distance from the centerline over the x-axis of centerline point index. The segmentation of the guide wire tip is performed effectively by analyzing this function instead of 2-dimensional image processing. Using the results of segmentation, a region of interest is determined and a local fine registration is performed, again by calling registration component 578. The center point of the guide wire tip, as well as the index in the centerline closest to the center point are obtained. Vector representation component 574 then performs a vector representation of the guide wire tip using a fast algorithm utilizing the suggested parameterization, or using optimal path search techniques on the image plane. Once the detection is complete, the guide wire tip can be shown on the reference image, the 3-dimensional model or other images. Numerical data, such as the direction and curvature of the artery at the guide wire endpoint location, distance to bifurcation, or others, can be provided as well. Once the guide wire is detected, tracking it in the following frames is performed using local registration of a small segment of the image, since the general location of the guide wire tip is known.

Therapeutic device detection component 580 detects the devices using one or more, preferably two markers placed on the device, the markers showing like dark points in an x-ray image. The device is identified in a current image, by identification component 584. First a filtering, enhancing the dark points is used, and then thresholding is performed over all pixels in the image. The filters are, for example Laplacian of Gaussian, filters based on analysis of aigenvalues of Hessian matrix, or the like. This results in clusters of pixels that passed a predetermined threshold values. Normally the marker clusters and few "confuser" clusters are present. The clusters are labeled, assigned with a score that takes into account all scores of pixels in the cluster, and a representative pixel of every cluster is selected. Clusters which are small relatively to other clusters are discarded. The parameters of cluster detection are tuned to minimize the number of detected clusters while preserving the marker clusters. Next, pairs of clusters are considered, since the device is preferably represented in an x-ray image by two markers. Therefore, each pair represents a possibility that the two clusters of the pair indeed represent the two markers. The score assigned to each pair is a product of the two cluster scores. Typically, the pair with the highest score is assumed to represent the markers. However, if an estimation exists for the expected distance between the markers, then the score is multiplied by a function of the ratio between the real distance between clusters and the expected distance. As a further step, the values are normalized to make the sum of all pair estimations be equal to one. However, marker detection based on one frame might be insufficient. Therefore, alternatively two or more successive frames are used. In a one non-limiting example of the current invention, let M denote the number of available pairs in the first frame, and N denote the number of available pairs on the second frame. The probabilities of pairs 1 . . . M to represent the device in the first frame are denoted by p1, . . . , pM and the probabilities of pairs 1 . . . N to represent the device in the second frame are denoted by q1, . . . , qN. The device markers correspond to two pairs on both frames, therefore a pair of pairs of points is required, i.e., a quartet. In order to locate the correct pair in the first and in the second frame, an M×N matrix R is constructed, where the (i,j) element is $r(i,j) = p_i * q_j * f(i,j)$, where $f(i,j)$ is some function describing the similarity between the i-th pair on the first frame and the j-th pair on the second frame. In particular $f(i,j)$ reflects how the distance between the points in the pair is preserved. The $r(i,j)$ criterion filters out incorrect pairs. Other components of the $r(i,j)$ function may include the cluster sizes and distances to the a reference skeleton.

If the total sum of the elements of matrix R is below a predetermined threshold, the pair of frames is declared to be inconsistent, and discarded. If the two frames constitute a part of a longer process with no definite conclusions, the process is reset. If the total sum of the elements of matrix R is above the predetermined threshold, the probabilities for pair i in one of the frames to represent the markers is estimated by:

$$p_i(\text{forward}) = \sum_{j=1}^{N} r(i, j) \text{ i.e.,}$$

the probability that pair i of clusters in the first frame represents the markers is equal to the sum of probabilities that this pair corresponds to all other pairs in the following frame.

Similarly for pair j in the second frame, in relation to the first frame $$q_j(\text{back}) = \sum_{i=1}^{M} r(i, j).$$

Thus, on each frame in the middle of a sequence there are therefore two additional estimations for each pair of clusters, one marked with "forward", obtained through comparison to the following frame, and another, marked with "back", obtained through comparison to the closest former frame. When we have the sequence of fluoro frames, for each frame, beginning from the second, we may use the estimation for the pairs $q_j(\text{back})$, instead of $q_j$, thus accumulating the information from the previous frames. In a similar way starting from the last frame we may use $p_i(\text{forward})$ instead of $p_i$ Then, for each pair in each frame, the two estimations are combined into one:

$$p_l == \frac{p_l(\text{forward}) * q_l(\text{back})}{\sum_{k=1}^{N} p_k(\text{forward}) * q_k(\text{back})}$$

Then, if for some pair l, $p_l$ exceeds a predetermined confidence threshold, the markers are declared to be represented by pair l.

The preferred process starts by analyzing two adjacent fluoroscopic frames. If markers are identified (for one pair l in one of the frames, $p_l$ exceeds the predetermined threshold) the process is terminated. Otherwise, the process is generalized by adaptation to considering an additional fluoroscopic frame to the sequence and $p_l$ values are recalculated for the three frames, using the described process. If markers are not identified, another additional frame is added. If after adding a predetermined number of frames, markers identification is not achieved, the sequence is discarded and the process is initialized with a new pair of frames.

Therapeutic device tracking component 588 is activated once a definite recognition of the device is achieved. The system switches to tracking the device, which is a task that requires less processing power and therefore performed in real-time. In order to be effective, tracking a device should take less time than the period between the acquisitions of two consecutive images. Tracking is performed by analyzing successive frames and tracking the identified markers. On the tracking phase, the component receives a current frame Fc where the two markers are to be found and a previous frame Fp with known marker coordinates M1 and M2. Small areas Wp1 and Wp2 around locations M1 and M2 are selected on image Fp and larger areas Wc1 and Wc2 around the locations M1, M2 are selected on image Fc. The radius of the large areas estimates a maximal possible marker movement between frames Fp and Fc. Areas Wp1, Wp2, Wc1 and Wc2 preferably pass preprocessing filtering enhancing dot-like features, for example, Laplacian of Gaussian filter, filters based on analysis of aigenvalues of Hessian matrix, or the like. Then correlations between Wp1 and Wc1 and the correlation between Wp2 and Wc2 are performed. Preferably normalized correlation, phase correlation or gradient vector field correlation are used, but the correlation is not limited to a specific type. As a result, two correlation surfaces C1 and C2 are obtained. Peaks on the correlation surfaces represent areas within Wc1 and Wc2 that are candidates to be the current location of the markers. Let T=(t1,t2, . . . , tn) denote the set of prominent local maxima found on C1 and S=(s1,s2, . . . , sm) denote the set of prominent local maxima found on C2. Every peak has a score equal to the corresponding correlation values $C1(t_i)$ and $C2(s_j)$. Every pair $(t_i, s_j)$ of possible shifts of the two markers from the previous image to the current image passes a test for a movement consistency criterion giving a pair score $V(t_i, s_j)$. In particular $V(t_i, s_j)$ can be a measure of difference between vectors M2−M1 and $s_j - t_i$, i.e. the distance and direction of the location of the markers should be preserved between the frames. Every pair gets an aggregated score combining $C1(t_i)$, $C2(s_j)$ and $V(t_i, s_j)$, for example $p_l = (C1(t_i) + C2(s_j)) * V(t_i, s_j)$. The pair that obtained the maximal aggregated score is identified as the shifts of the markers and the markers locations on the current frame are calculated using the previous locations and the shifts. As mentioned above, binary images showing the tracked device are used in the registration process, as the device enhanced image (D1) discussed in association with FIG. 5 above.

As mentioned above, the present invention uses an improved vessel resemblance operator IVR(p). The conventional vessel resemblance operator VR(p) uses the aigenvalues of the Hessian matrix to enhance the pixels p, where the gray levels have a large positive second derivative in one direction and a small second derivative in the orthogonal direction. In order to better discriminate tubular features like vessels, from step-like features (such as, for example boundary of diaphragm) an improved vessel resemblance operator is used, requiring small gradient in addition to the properties of the second derivatives, as detailed above. The additional gradient term in the expression for the improved vessel resemblance IVR(p) might have, for example the following form: IVR(p)=VR(p)·F(|g|), Where F(|g|) is equal to 1 for a zero gradient magnitude |g|, and decreases as the gradient magnitude increases.

Figure 7:
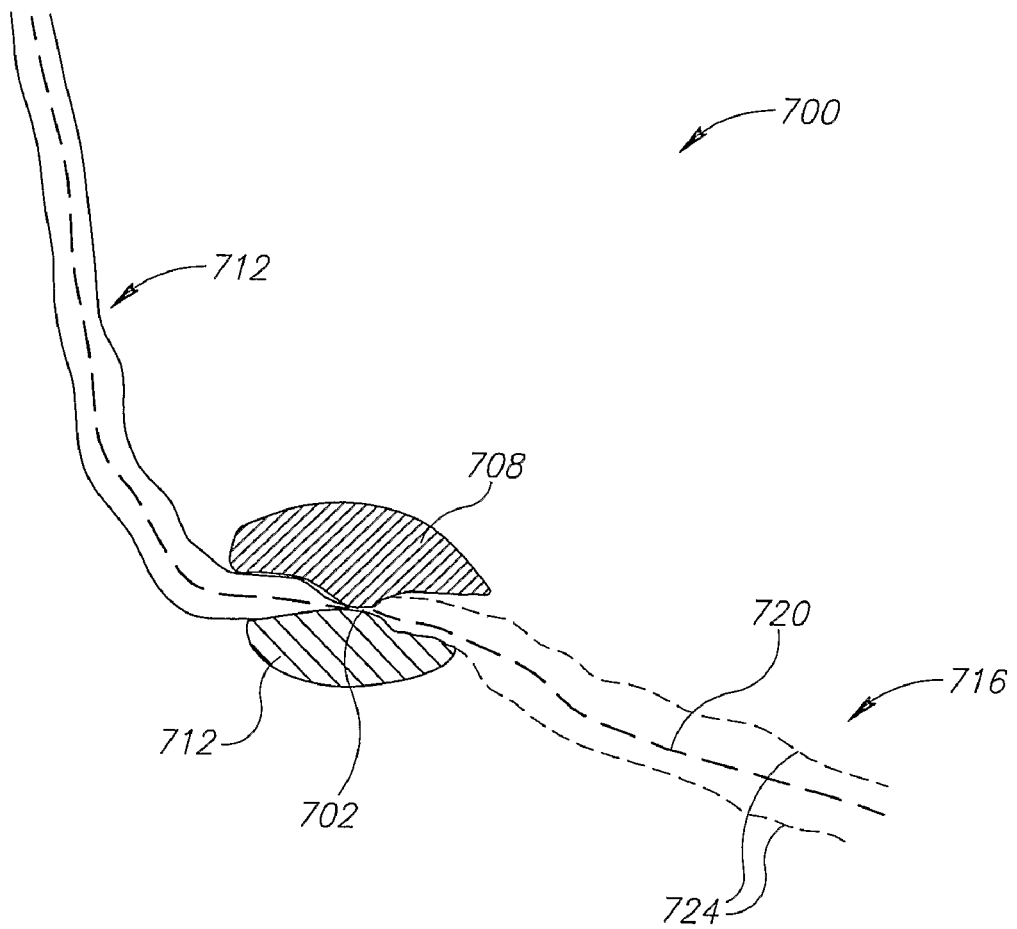
FIG. 7 is an illustration of a usage of the disclosed invention in a of Chronic Total Occlusion.

The above presented method and apparatus can be used for Chronic Total Occlusion (CTO) or near total occlusion situations. Referring now to FIG. 7, showing the advantages of the above detailed method and apparatus for treating Chronic Total Occlusion (CTO). In a CTO situation, the artery, generally referenced 700 is occluded in area 702. The occluding sediments may comprise any combination of calcified plaque 708 and non-calcified plaque 712. When an angiogram of the artery is taken, for example during an operation, only part 712 of the artery, i.e. the part proximal to occlusion area 702 is viewed. Area 716, which is distal to occlusion area 702 receives no blood follow, and therefore no contrast material. Thus area 716 is not viewed in the angiogram. When a physician wishes to drill through occlusion area 702 in order to release the occlusion, not being able to see the vessel morphology beyond occlusion area 702 is a problem. If the physician does not drill along the centerline of the vessel, he may perforate the vessel, which when combined with the restored blood flow is a dangerous situation. Thus, if at least the centerline of the distal part pf the vessel can be seen, then navigation of the driller through occlusion area 702 and further in the distal direction can be continued as described above. For CTO situations, at least the centerline of area 716, referenced as 720, and possibly the vessel walls referenced as 724 should be available from a previously constructed three-dimensional model, preferably constructed from images taken by another modality than an angiogram, such as a CT. Using such a modality enables the imaging, and hence the modeling of both proximal and distal parts (relatively to the occlusion area) of the artery, wherein the angiogram shows only the proximal parts. Thus, it will be apparent to a person of ordinary skill in the art that the modality used in the diagnostic stage should be a different one from the modality used in the therapeutic stage, at least in the ability to capture blood vessels through which blood does not flow. Such modality can be a CT, a Magnetic Resonance Imaging (MRI) modality or another modality currently known or that will be developed in the future. Thus, by registering an image comprising a device and part 712 which is viewable in an angiogram, with the same part as appeared in an image taken from the three-dimensional model showing also area 716, a complete image of the vessel, comprising areas 712, 702, 716 and a device within the vessel is achieved. Having the unified image, the physician can then navigate the driller along the artery according to the morphology of the vessel as described above, penetrate occlusion area 702 and avoid puncturing areas of the vessel distal to occlusion area 702, such as area 716.

Moreover, once a three-dimensional model of the artery, showing also the plaque is available, the physician can view one or more cross sections of the artery on or near the occluded area, and choose to drill, or to start the drilling, at the area of the cross section in which the plaque layers are thinnest, which is easier. Such cross sections are also available in a model generated from CT imaging.

Figure 8A:
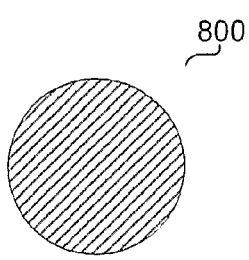
FIGS. 8A, 8B, and 8C show schematic illustrations of cross sections of an occlusion area of an artery.
Figure 8B:
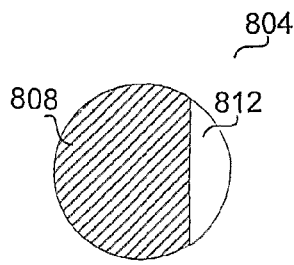
Figure 8C:
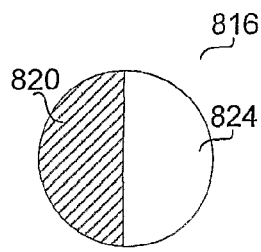

Referring now to FIGS. 8A, 8B, 8C, showing illustrations of consecutive lateral cross sections of an artery. FIG. 8A shows a lateral cross section of the artery and its surroundings, wherein the whole cross section is occluded with sediments, FIG. 8B shows a cross section of the artery, wherein the cross section generally referenced 804 is distal to the cross section of FIG. 8A, and FIG. 8C shows a cross section 816 of the artery, generally referenced 816 which is further distal to the cross section of FIG. 8B. Cross section 804 comprises an occluded area 808 and free area 812, and cross section 816 comprises occluded area 820 and free area 824. Studying cross sections 800, 804, 816 shows that the occlusion is thicker on the part that appears on the left hand side of cross sections 800, 804, 816, so a physician is more likely to drill into the occluded area on the right hand side, where the occlusion is thinner.

Figure 9:
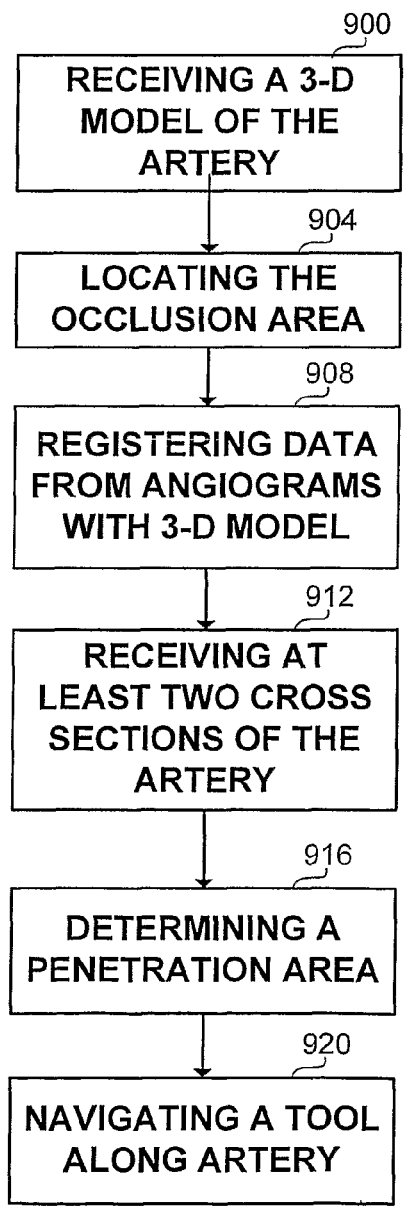
FIG. 9 is a schematic flowchart of a method for drilling a Chronic Total Occlusion, according to a preferred embodiment of the disclosed invention.

Referring now to FIG. 9, showing a flowchart of A method for applying the disclosed invention to CTO situations. At step 900 a three-dimensional model of the artery preferably constructed during the diagnostic stage is received by a system constructed in accordance for example with FIG. 6 above. At step 904, the driller or another device is detected and tracked along the artery and until the occluded area according to steps 272, 274, 276, 278, 282 and 286 of FIG. 4. At step 908, the data from the angiogram is registered with the three-dimensional data received at step 900. Steps 904 and 908 are described in a schematic manner, wherein the full description is identical to the description provided in association with FIG. 4 above. Registration step 908 thus comprises registering a current image showing only the device or at least two device markers with a last injection image showing the parts of the tubular organ proximal to the occlusion, and registering the last injection image with an image showing areas of the tubular organ proximal to the occlusion, and areas of the tubular organ distal to the occlusion. The last injection image shows nothing of the areas immediately distal to the occlusion area. Alternatively it shows the area proximal to the tubular organ in a manner distinct from the distal part, due to little or no blood flow through the part.

Optionally, at step 912 at least two cross sections of the artery are received, and a preferred point or area for penetrating the occlusion is determined. At step 916, optionally a penetration area or penetration point is determined using the cross sections obtained at step 912. At step 920, the tool, such as the driller penetrates the occluded area optionally at or near the point or area determined at step 916, and is further navigated distally through the occluded area and along the artery as detailed in association with FIG. 4 above.

The presented method utilizes the disclosed invention for treating situations, such as CTO in which a tubular organ is imaged only partly in a first modality, such as an angiogram. The method and apparatus aid the navigation of a device within an occluded tubular organ. The method utilizes a three dimensional model, showing also parts not imaged by the first modality, and generates a unified image representing the device and parts both distal and proximal to the occlusion, to enable navigation within the occluded vessel through the occluded area. It will be appreciated that the disclosed invention can also be applied to situations of near total occlusion, wherein the parts of the tubular organ distal to the occluded area are distinguished from the areas proximal to the occlusion area by demonstrating a weaker flow, notable for example in an angiogram by a lighter (or darker, depending on the imaging modality) shade. Alternatively, if a partial occlusion exists over a section of the tubular organ, then letting enough contrast material flow through the partial occlusion to the part distal to the occlusion, can generate a non-continuous image of the tubular organ, i.e. the tubular organ may appear as though it ends at a first (proximal) arbitrary point and resumes at a second (distal) arbitrary point. Thus, the area immediately distal to the occlusion point appears insufficiently distinguishable from background, or not shown clear enough, is much narrower, or is hard to detect, so that navigation according to its direction is not enabled.

It will also be appreciated that the invention is not limited to angiograms showing the device or the three-dimensional model being constructed from CT images. Rather, any modality such as MRI or any other modality currently known or that will be developed in the future, which can supply at least two images for constructing three dimensional model of parts of the tubular organ both proximal and distal to the occlusion area can be used to construct the model, and any imaging modality showing the device and/or the tubular organ can be used in the navigation. It will also be apparent the invention is not limited to navigating a driller, rather any required device can be navigated through the occlusion area using the disclosed invention.

Additional steps can be added to the method for enhancing the navigation within the artery, for example analyzing the direction of the parts distal to the occluded area and showing an arrow or another indication for the recommended advancement direction, an automatic analysis of the preferred part of the cross section through which the drilling should be performed, an automatic navigation tool for navigating the device within the tubular organ, such as a magnetic navigation system, for example Stereotaxis NIOBE® Magnetic Navigation System manufactured by Stereotaxis of St. Louis, Mo., USA. If such a navigation system can manipulate a device both in the required direction, and in the preferred part of a cross section of the tubular organ, then providing guiding directions based on the combined image to such system allows for safe automatic navigation through the occluded area. It will be apparent that corresponding components should be added to an apparatus performing the disclosed method for implementing or enabling the abovementioned steps.

The proposed invention discloses a method and apparatus for positioning and guiding a device in a tubular organ. The invention discloses an optional diagnostic stage in which a model of the tubular organ is constructed, and a therapeutic device and a location for the device are recommended to the physician. Alternatively, the user can receive a model from an external source. Then, at a therapeutic stage, the apparatus employs the method to automatically register images captured during the therapeutic stage with the model, thus supporting detecting, tracking, navigating the device within the tubular organ. The system further enables displaying the device within the tubular organ along with relevant measurement data. The proposed method overcomes difficulties in the registration, resulting from geometric distortions and differences in content between images taken at the diagnostic stage and images taken at a therapeutic stage. The apparatus uses x-ray or another imaging modality during the therapeutic stage, although most tubular organs, such as vessels are not visible in x-ray images. The system does not require additional equipment in excess of the equipment currently required for the relevant types of procedures. Additionally, the system minimizes the need for harmful contrast material injections and radiations to the subject.

The proposed system uses x-ray images, in which the tubular organ is not visible during the therapeutic stage, or not fully or clearly enough shown when contrast material is used. However, other modalities can be used as well. If a modality that does show the tubular organ is used, the process will be greatly simplified. The description of the components presented above suggests a possible implementation. It is clear that multiple other divisions of the system into components, which perform different parts of the methods and cooperate in different ways, or usage of other components for carrying out the disclosed methods can be employed as well. It will be appreciated by persons skilled in the art that the present invention is not limited to what has been particularly shown and described hereinabove. Rather the scope of the present invention is defined only by the claims which follow.

What is claimed is:

1. A method for displaying an image of a device within an occluded tubular organ of a subject, for assisting in navigating the device through an occluded area of the tubular organ, the image representing the device, the occluded area of the tubular organ, an at least one part of the tubular organ proximal to the occluded area of the tubular organ, and an at least one part of the tubular organ distal to the occluded area of the tubular organ, the method comprising:
    registering a current image taken by an imaging modality showing at least two points of the device, with a last injection image, the last injection image imaging an at least one part of the tubular organ proximal to the occluded area, and a part immediately distal to the occluded area appearing insufficiently distinguishable from background;
    registering the last injection image with a reference image showing the occluded area, an at least one part of the tubular organ proximal to the occluded area, and an at least one part of the tubular organ distal to the occluded area;
    fusing information from the current image, the last injection image and the reference image, to obtain a combined image comprising the device, the occluded area of the tubular organ, an at least one part proximal to the occluded area of the tubular organ, and an at least one part distal to the occluded area of the tubular organ.

2. The method of claim 1 wherein the reference image is constructed from a reference source, the reference source constructed from images taken by a second imaging modality.

3. The method of claim 2 wherein the second imaging modality is a Computerized Tomography imaging device.

4. The method of claim 1 further comprising a step of navigating the device along the tubular organ using the at least one combined image to penetrate the occluded area.

5. The method of claim 1 wherein the imaging modality is an angiogram.

6. The method of claim 1 further comprising the steps of:
    receiving at least two images of at least two cross sections of the tubular organ;
    determining a penetration area; and
    penetrating the occluded area at the penetration area.

7. The method of claim 6 wherein the at least two cross sections are constructed from the reference source.

8. The method of claim 1 when used for penetrating a chronic total occlusion.

9. The method of claim 1 when used for penetrating a chronic near total occlusion.

10. An apparatus for aiding the navigation of a device within a an occluded tubular organ of a subject, the apparatus comprising:
    at least one detection component for detecting on an image the device within the tubular organ of the subject;
    at least one registration component for: registering a current image taken by an imaging modality showing at least two points of the device, with a last injection image, the last injection image imaging an at least one part of the tubular organ proximal to the occluded area, and an area immediately distal to the occluded area appearing insufficiently distinguishable from background; and registering the last injection image with a reference image showing the occluded area, an at least one part of the tubular organ proximal to the occluded area, and an at least one part of the tubular organ distal to the occluded area; and
    a display preparation component for rendering a combined image showing the device, the occluded area of the tubular organ, an at least one part of the tubular organ proximal to the occluded area and an at least one part of the tubular organ distal to the occluded area.

11. The apparatus of claim 10 wherein the tubular organ is an artery suffering from chronic total occlusion.

12. The apparatus of claim 10 wherein the tubular organ is an artery suffering from chronic near total occlusion.

13. The apparatus of claim 10 further comprising an automatic navigation system for automatically navigating the device within the tubular organ through the occluded area.

14. A non-transitory computer-readable medium containing a set of instructions for a general purpose computer, the set of instructions comprising:
    registering a current image taken by an imaging modality showing at least two points of a device, with a last injection image, the last injection image imaging an at least one part of a tubular organ proximal to an occluded area of the tubular organ, and an area immediately distal to the occluded area appearing insufficiently distinguishable from background;
    registering the last injection image with a reference image showing the occluded area, an at least one part of the tubular organ proximal to the occluded area, and an at least one part of the tubular organ distal to the occluded area;
    fusing information from the current image, the last injection image and the reference image, to obtain a displayed image comprising the device, the occluded area of the tubular organ, an at least one part proximal to the occluded area of the tubular organ, and an at least one part distal to the occluded area of the tubular organ.

* * * * *